(12) United States Patent
Wang

(10) Patent No.: US 7,581,851 B2
(45) Date of Patent: Sep. 1, 2009

(54) SCENTED LIGHTING DEVICES AND SYSTEMS, AND METHODS FOR MAKING THE SAME

(76) Inventor: Jessica Wang, 16F-3, No. 70, Sec. 2, Tun-Hua South Road, Taipei (TW)

( * ) Notice: Subject to any disclaimer, the term of this patent is extended or adjusted under 35 U.S.C. 154(b) by 207 days.

(21) Appl. No.: 11/029,036

(22) Filed: Jan. 3, 2005

(65) Prior Publication Data

US 2006/0147353 A1    Jul. 6, 2006

(51) Int. Cl.
  *F21V 23/00* (2006.01)
(52) U.S. Cl. .................. 362/249.01; 362/643; 362/644; 362/253; 362/806
(58) Field of Classification Search ............... 362/249, 362/391, 392, 806, 643, 644, 253; 392/391, 392/392, 393; 422/123–125, 305–307
See application file for complete search history.

(56) References Cited

U.S. PATENT DOCUMENTS

| | | | | |
|---|---|---|---|---|
| 555,320 | A * | 2/1896 | Knowles ..................... | 362/249 |
| 1,706,939 | A * | 3/1929 | Rosenthal ................... | 422/125 |
| 2,468,164 | A * | 4/1949 | Brewster .................... | 392/393 |
| 4,757,099 | A | 7/1988 | Hoshino et al. ............ | 523/102 |
| 5,233,680 | A | 8/1993 | Fussell ....................... | 392/390 |
| 5,577,156 | A * | 11/1996 | Costello ..................... | 392/390 |
| 5,861,128 | A | 1/1999 | Vick et al. .................. | 422/124 |
| 6,258,871 | B1 | 7/2001 | Brown, III .................. | 523/102 |
| 6,334,974 | B1 | 1/2002 | Chen ..................... | 264/328.18 |
| 6,503,459 | B1 * | 1/2003 | Leonard et al. ............. | 422/125 |
| 6,566,416 | B2 | 5/2003 | Brown, III .................. | 523/102 |
| 6,935,762 | B2 * | 8/2005 | Van Dyn Hoven ......... | 362/237 |
| 2005/0163649 | A1 * | 7/2005 | Friedrich et al. ............. | 422/1 |

* cited by examiner

*Primary Examiner*—Sharon E Payne
(74) *Attorney, Agent, or Firm*—Seed IP Law Group PLLC

(57) ABSTRACT

Lampholders formed from materials comprising scented compounds that are more volatile when warm than when at ambient temperature to generate a desired scent during use, along with lighted displays incorporating such lampholders and methods for making such lampholders, are shown and described.

12 Claims, 4 Drawing Sheets

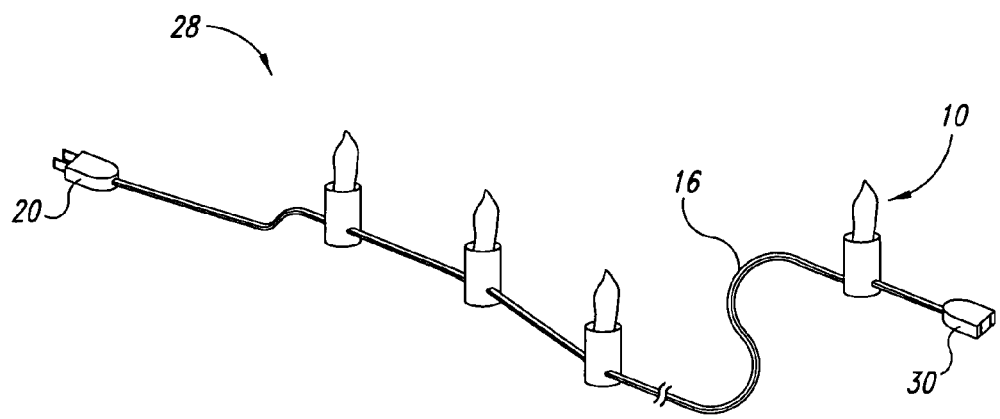
FIG. 3
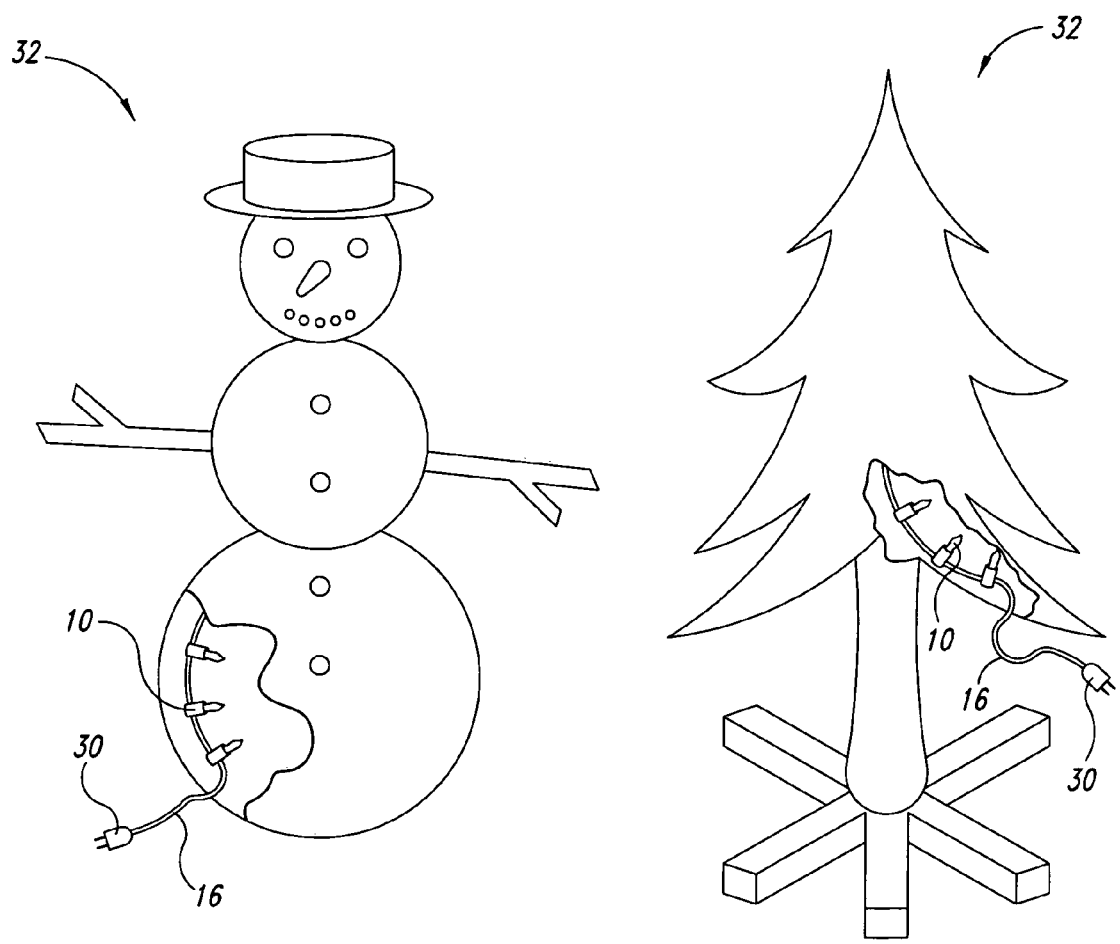
FIG. 4A
FIG. 4B

SCENTED LIGHTING DEVICES AND SYSTEMS, AND METHODS FOR MAKING THE SAME

BACKGROUND OF THE INVENTION

1. Field of the Invention

The present invention relates to electric lighting elements, light strings and lighted displays, and to methods of manufacturing the same.

2. Description of the Related Art

Smell sometimes can play as large a role as sight and sound typically do in creating and remembering an experience. For example, the smell of food cooking, the ocean, popcorn, or a pine tree often brings back memories of certain events or locations as fast or faster than the associated sights and sounds.

As a consequence, air fresheners and other scented articles, both natural and synthetic, have been developed to help create such an environment or bring back such a memory when the real smell is not available. Typically these devices are designed to be attractive or inconspicuous; for example, non-electric air fresheners may be designed to be adhered to the back or bottom of an article of furniture and electric air fresheners may be flat, small and light colored to blend in with the wall when plugged in.

Most air fresheners have a housing with a cavity in it that retains a scented fluid or gel. The fluid typically is held in a reservoir or absorbed in a porous body, while the gel may have enough structural integrity to be attached or coupled to the housing. When the scented fluid or gel evaporates, the fluid is refilled or the gel replaced to cause the air freshener to function again.

The scented gel or fluid typically is volatile—which is desired for an air freshener in order to generate odor—but, as a result, the scented fluid or gel often dissipates faster than desired. Evaporating too quickly results in too strong a scent being generated in the surrounding area and undesirably frequent replacement or refilling or replacement of the scented fluid or gel. Adjustable openings often are used to prevent too much odor from escaping the air freshener housing; however, this may not solve the problem of frequent refill or replacement.

BRIEF SUMMARY OF THE INVENTION

The present invention is directed toward devices and systems using electric lighting elements, light strings and lighted displays, and other lighted articles used not only to create a desired visual effect, but also to generate a desired scent during use. In particular, the invention is directed toward scented lampholders and to light strings and lighted displays incorporating scented lampholders. For the purpose of this disclosure, the term "lampholder" can be interpreted to include thy lamp base, the socket, and/or the socket base, depending on the construction of the particular lampholder.

In one disclosed embodiment, the invention is directed toward a lampholder having a body configured to be physically coupled to a lighting element and at least one electrical conductor such that the lighting element is operatively electrically coupled to the at least one conductor. At least part of the body is made from a material comprising a compound having a desired scent. The scented compound has an elevated rate of vaporization from the material when the lampholder is in a heated state due to being engaged with an illuminated lighting element. The elevated rate of vaporization is significantly greater than a reduced rate of vaporization of the scented compound from the material occurring when the lampholder is not in the heated state.

In another disclosed embodiment, the material comprises a compound having a desired scent and having a first rate of vaporization from the material when the lampholder is in a heated state due to being engaged with an illuminated lighting element. The first rate of vaporization is great enough that the desired scent can be noticed in the vicinity of the lampholder when the lampholder is operating. The scented compound has a second rate of vaporization from the material when the lampholder is not in the heated state. The second rate of vaporization is low enough that the desired scent is at least substantially unnoticeable in the vicinity of the lampholder when the lampholder is not operating.

The present invention is also directed toward methods of making such devices and systems. In one disclosed embodiment, a method for making a lampholder for a lighting display that generates a desired scent during operation includes the steps of combining a polymeric material and a scented compound to form a scented polymeric material having a desired scent; and forming the scented polymeric material into at least one lampholder part.

In another disclosed embodiment, a method for making a lampholder for a lighting display that generates a desired scent during operation includes the steps of melting a polymeric material to form a liquid polymeric material; adding a scented compound to the liquid polymeric material to form a liquid scented polymeric material having a desired scent; forming the liquid scented polymeric material into the shape of at least one lampholder part; and cooling liquid scented polymeric material until the lampholder part is solid.

The present invention is also directed toward lighting systems incorporating such lampholders.

BRIEF DESCRIPTION OF THE SEVERAL VIEWS OF THE DRAWING(S)

In order to assist understanding of the present invention, embodiments will now be described, purely by way of non-limiting example, with reference to the attached drawings, in which:

FIG. 3 is an isometric view of a light string according to an illustrated embodiment of the present invention.

FIGS. 4A and 4B are isometric views of a pair of light displays according to an illustrated embodiment of the present invention.

DETAILED DESCRIPTION OF THE INVENTION

The present invention is directed toward devices and systems for using electric lights, light strings and lighted displays, or other lighted articles, to generate a desired scent during use, and to methods of making such devices and systems. The following is a detailed description of a few illustrative embodiments. The drawings are provided to clarify the description, and may not be to scale.

Figure 1:
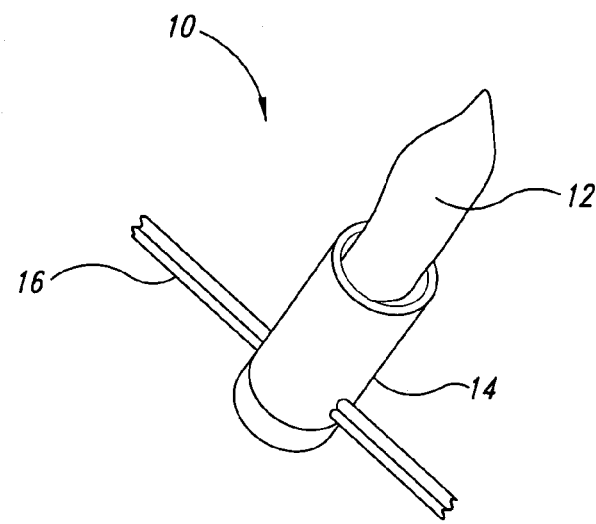
FIG. 1 is an isometric view of a lampholder, a lighting element and a portion of a conductor, according to one illustrated embodiment of the present invention.

FIG. 1 illustrates a light 10 for a light string, lighted display or the like. A typical light 10 may be made up of a lighting element 12 and a lampholder 14, which are coupled to a conductor 16 carrying many lights along its length.

Figure 2:
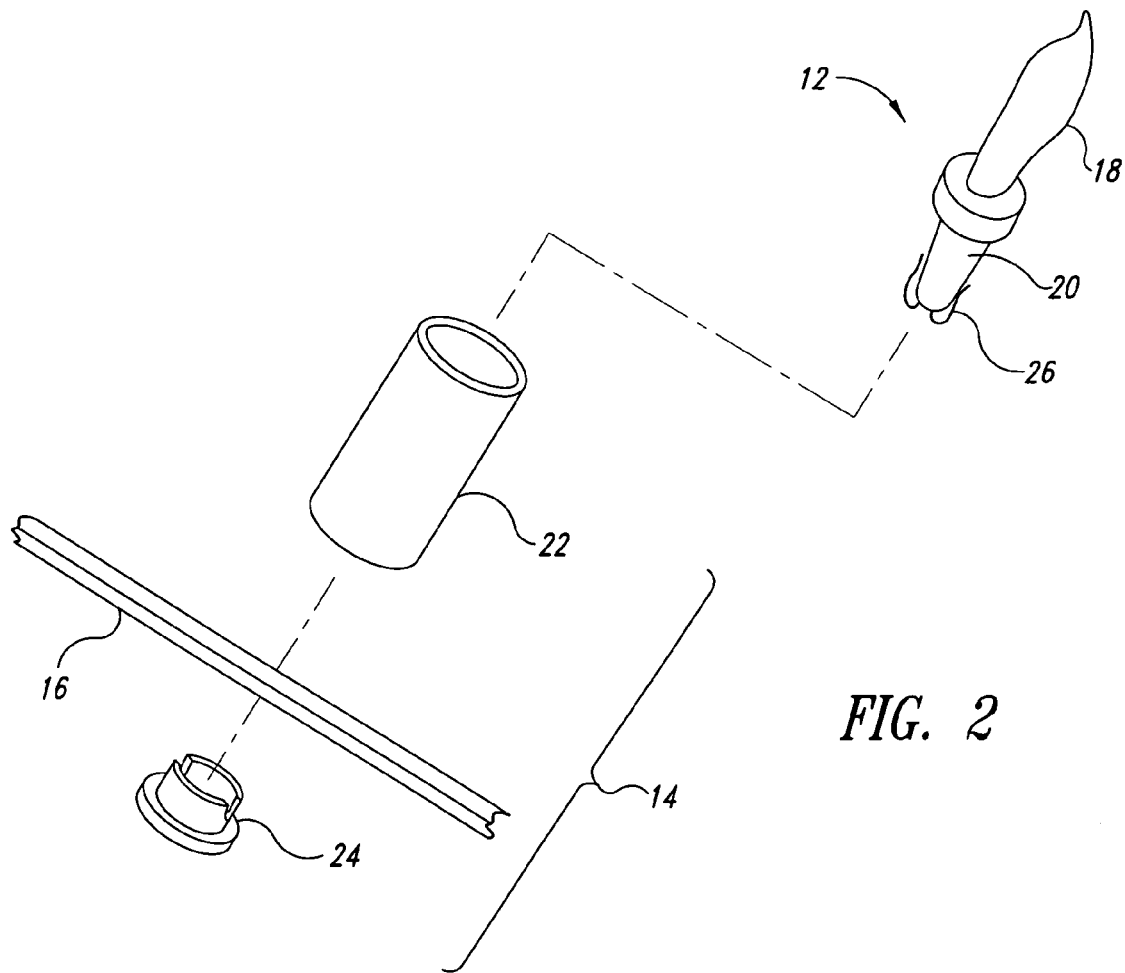
FIG. 2 is an exploded view of the lampholder, lighting element and portion of conductor of FIG. 1.

As better illustrated in FIG. 2, the lighting element 12 may be made up of a lamp 18 and a lamp base 20; and the lampholder 14 may be made up of a socket 22 and a socket base 24. A pair of leads 26 on the lighting element 12 can be coupled to one or more wires in the conductor 16 via contacts in the lampholder 14 such that the bulb 18 illuminates when the conductor is energized. The inventor appreciates that some of these details can be modified without deviating from the spirit of the invention, and that an individual of ordinary skill in the art having reviewed this disclosure will appreciate modifications that could be made to the illustrated embodiment.

FIG. 3 illustrates a light string 28 according to one particular embodiment of the present invention. The illustrated light string 28 extends between a pair of electrical connectors 30, and may contain 150 lighting elements 10, 300 lighting elements, or any other number desired by the manufacturer. Likewise, the lighting elements 10 can be incandescent bulbs, clear or colored bulbs, flashing bulbs, or any other suitable bulb or lighting element. In addition, the light string 28 can be in the form of a single string, as illustrated; however, the inventor appreciates that swag lights, net lights and other configurations would also work with the present invention.

FIGS. 4A and 4B illustrate two particular lighted displays 32 according to disclosed embodiments of the present invention. The lighted display 32 can have a solid frame or planar substrate giving it a desired shape, such as the illustrated snowman and tree. One or more light strings 28 can be routed about and coupled to the frame or extended through the substrate, or can otherwise be coupled to the lighted display 32. The lighted display 32 can be left uncovered, or can be covered with a layer of material to create a desired affect when the lighted display is illuminated.

Figure 7:
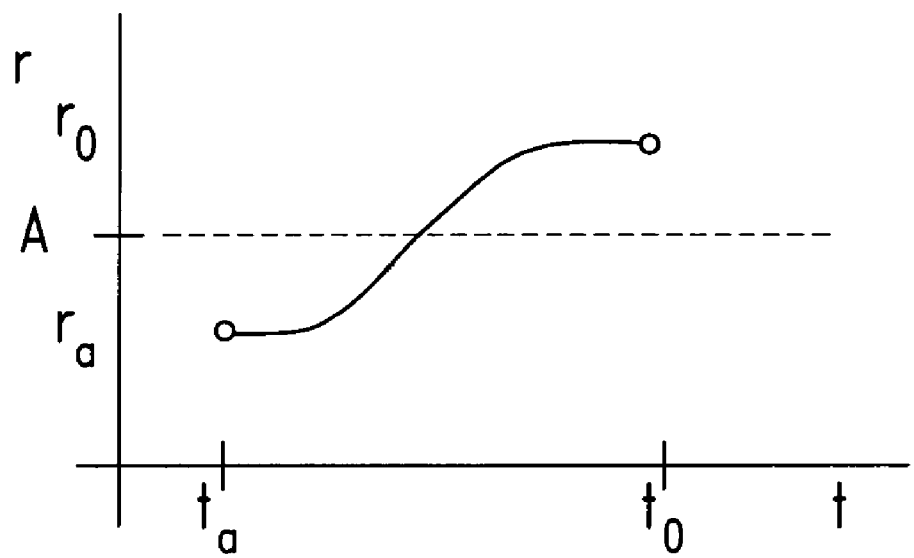
FIG. 7 is a graph plotting the rate at which scented compound vaporizes from the plastic of the lampholder, as a function of the temperature of the plastic.

In each of the above-described embodiments, the device or system incorporates a lampholder made from a material that generates a significant amount of a desired scent when the lighting element, light string or lighted display is operating, but does not generate a significant amount of the desired scent when the same is not operating. As reflected in FIG. 7, the concentration of the scented compound is selected such that the rate the scent is generated "$r_o$" at operating temperature "$t_o$" is at or above the concentration sufficient for individuals in the vicinity of the lights to readily appreciate the scent "i.e., >A", while the rate the scent is generated "$r_a$" at ambient temperature "$t_a$" during non-use is below the concentration necessary for individuals in the vicinity of the lights to readily appreciate the scent "i.e., <A".

The particular scent selected for a particular device or system can complement the design of the lighted display, such as by using a pine scent for the lights on a tree or a peppermint scent for the lights on a candy cane, or can merely be an attractive scent, such as the scent of mulled spices on a Christmas-related display or the scent of pumpkin pie on a Thanksgiving-related display. An individual of ordinary skill in the art having reviewed this disclosure will appreciate the variations that could be made to these examples without deviating from the spirit of the invention.

Figure 5:
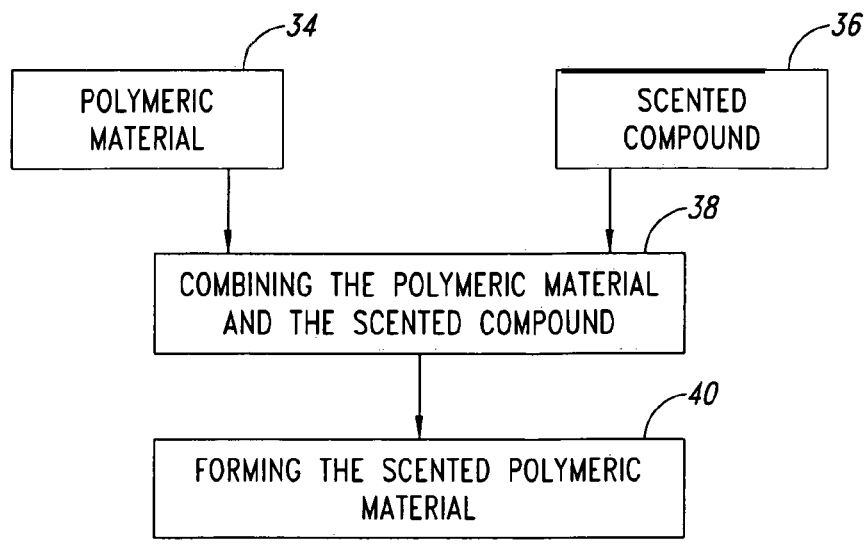
FIG. 5 is a flow chart illustrating a method for making a lampholder according to one disclosed embodiment of the present invention.

FIG. 5 illustrates a method for making an article having a desired scent. The illustrated method begins with a polymeric material 34 and a scented compound 36. The method then involves the step of combining 38 the polymeric material 34 and the scented compound 36. The compounds may be combined in solid form (e.g. pellet, powder, etc.) or in liquid form, or a combination thereof (e.g. adding a powder to a liquid). The ratio of scented compound 36 to polymeric material 34 is selected to provide a desired amount of scent based on the use envisioned for the finished product (e.g. products for outdoor use may have more scented compound than equivalent products for indoor use).

Finally, the illustrated method involves forming 40 the scented polymeric material into a desired part. The part may be the lamp base 20, the socket 22 and/or the socket base 24. Again, an individual of ordinary skill in the art having reviewed this disclosure will appreciate how many parts to form from the scented polymeric material to obtain the desired amount of scent for a particular purpose, as more scented parts will obviously result in a stronger scent.

EXAMPLE 1

The inventor has practiced the present invention in several different ways, and provides herein a representative example of a method used to manufacture a scented device according to the present invention. In this particular example, the inventor used at least the following compounds: a resin, a fragrance diluter, a dispersing agent, a fragrance, a fragrance main agent, and an anti-oxidant. The procedure included the steps of: adding the fragrance to the fragrance diluter and stirring thoroughly; mixing in the dispersing agent, the anti-oxidant and the resin; and melting polypropylene pellets from an injection machine at a temperature between about 80~120 Celsius. The flame retardant polypropylene and the fragrance main agent mix ratio is between about 8:1~12:1 (ratio by weight). The pellets are then used to produce product by injection, as is generally understood in the art. An individual of ordinary skill in the art having reviewed this disclosure will appreciate that these compounds, ratios, temperatures and/or steps can be changed or supplemented without deviating from the spirit of the invention.

EXAMPLE 2

The inventor has practiced the present invention in several different ways, and provides herein another representative example of a method used to manufacture a scented device according to the present invention. In this particular example, the inventor mixed the flame retardant polypropylene with 1~2% fragrance, and then produced the product by injection, as generally understood in the art. As these two non-limiting examples reflect, there are many specific methods that could be used to carry out the present invention, and the inventor intends that this patent cover all such methods, not merely the examples provided. As such, the inventor submits the following claims to reflect the scope of the invention, which should not be limited by the examples provided.

Figure 6:
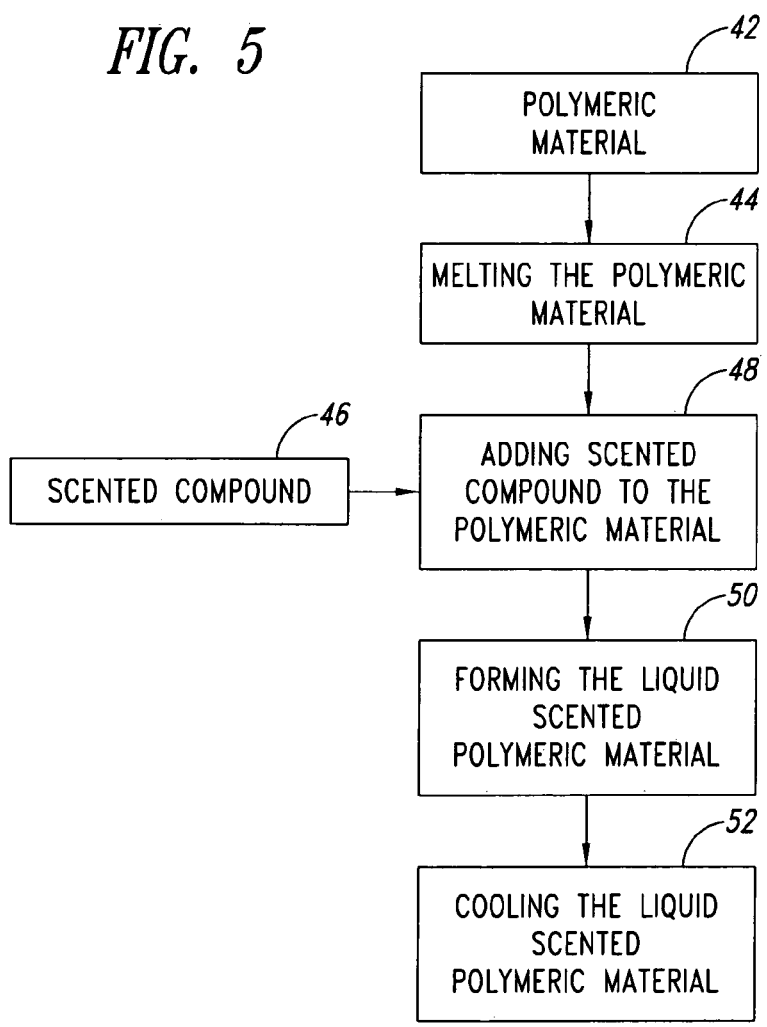
FIG. 6 is a flow chart illustrating a method for making a lampholder according to one disclosed embodiment of the present invention.

FIG. 6 illustrates a method for making scented lampholder parts according to another disclosed embodiment of the present invention. In this particular embodiment, the method begins by taking a polymeric material 42 and melting 44 the polymeric material. A scented compound 46 is added 48 to the melted polymeric material 42. The method continues with the step of forming 50 the liquid scented polymeric material into one or more of the parts of the lampholder. Finally, the illustrated method incorporates the step of cooling 52 the scented polymeric material to fix it in the shape of the desired lampholder part. An individual of ordinary skill in the art having reviewed this disclosure will appreciate the details involved in carrying out this method, and will appreciate the additions and modifications that could be made to the method without deviating from the spirit of the invention.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An electric lampholder for generating a desired scent when operating a lighting element, the lampholder comprising:
   an electric socket having at least one electrical conductor, the socket configured to be physically and electrically coupled to the lighting element such that the lighting element is operatively electrically coupled to the at least one conductor; and
   wherein the socket has a permanent shape and at least one portion of the socket is made from a material comprising a scented compound having a desired scent, the scented compound being present throughout the at least one portion of the socket, the scented compound having an elevated rate of vaporization from the material when the socket is in a heated state due to being in close proximity to the illuminated lighting element, the elevated rate of vaporization being significantly greater than a reduced rate of vaporization of the scented compound from the material when the socket is not in the heated state, the socket being in a solid state when the lampholder is in the heated state and configured to be physically and operatively used as an unscented electric socket after substantially all the scented compound evaporates.

2. The lampholder of claim 1 wherein the socket is configured to be physically coupled to a lighting element comprising an incandescent bulb.

3. The lampholder of claim 1 wherein the socket is coupled to a lamp base.

4. The lampholder of claim 1 wherein the socket is an assembly comprising at least two elements.

5. The lampholder of claim 1, farther comprising a contact for coupling the lighting element to the at least one conductor.

6. The lampholder of claim 1 wherein the heated state corresponds to when the temperatures of the lighting element and lampholder reach steady state.

7. An electric lampholder for generating a desired scent when operating a lighting element, the lampholder comprising:
   an electric socket having a rigid structure configured to be physically coupled to the lighting element and including at least one electrical conductor such that the lighting element is operatively electrically coupled to the at least one conductor; and
   wherein a material that forms the socket comprises a polymeric material and a scented compound having a desired scent, the scented compound being encapsulated in the rigid structure of the socket and having a first rate of vaporization from the material when the socket is in a heated state due to being proximate to the illuminated lighting element, the first rate of vaporization being great enough that the desired scent can be noticed in the vicinity of the lampholder when the lampholder is operating, the scented compound having a second rate of vaporization from the material when the socket is not in the heated state, the second rate of vaporization being low enough that the desired scent is at least substantially unnoticeable in the vicinity of the lampholder when the lampholder is not operating, at least the polymeric material maintaining integrity of the rigid structure of the socket during and after the scented compound has evaporated such that the socket remains configured to be physically and electrically coupled to the lighting element after substantially all the scented compound evaporates.

8. An electric lighted display for generating a desired scent during operation, the lighted display comprising:
   a plurality of lighting elements; and
   a plurality of lampholders, each lampholder having an electric socket including a permanent shape and operatively receiving one of the lighting elements therein;
   wherein the socket includes at least one conductor configured to electrically couple the lampholders and lighting elements to a source of electricity, at least a portion of each socket being made from a material comprising a scented compound having a desired scent, the scented compound having an elevated rate of vaporization from the material when the socket is in a heated state due to being proximate to an illuminated lighting element, the elevated rate of vaporization being significantly greater than a reduced rate of vaporization of the scented compound from the material when the socket is not in the heated state, the socket being solid when in the heated state and configured to remain physically and operatively coupled to the lighting element after substantially all the scented compound evaporates.

9. A lighted display for generating a desired scent during operation, the lighted display comprising:
   a plurality of lighting elements; and
   a plurality of lampholders, each lampholder having an electric socket operatively receiving one of the lighting elements therein;
   wherein the socket includes at least one conductor configured to electrically couple the lighting elements to a source of electricity, the socket having a permanent shape and being made from a material comprising a scented compound having a desired scent, the scented compound having a first rate of vaporization from the material when the socket is in a heated state due to being proximate to an illuminated lighting element, the first rate of vaporization being great enough that the desired scent can be noticed in the vicinity of the lampholder when the lampholder is operating, the scented compound having a second rate of vaporization from the material when the socket is not in the heated state, the second rate of vaporization being low enough that the desired scent is at least substantially unnoticeable in the vicinity of the lampholder when the socket is not operating, the shape of the socket remaining substantially intact as the scented material evaporates such that it remains configured to be physically and operatively coupled to the lighting element after substantially all the scented material evaporates.

10. The lighted display of claim 9 wherein each of the plurality of lighting elements include an incandescent light bulb configured to emit heat when illuminated, and wherein each of the plurality of lampholders include a lamp base and a contact portion configured to couple the lighting element to the at least one conductor.

11. A device comprising:
   an electric socket having a permanent shape and being configured to be coupled to a lighting element, the socket including:
   a base portion having walls projecting therefrom to form an at least partially cylindrical cavity having an open end, the base portion having one or more conductors, the open end being configured to receive the lighting element, wherein at least a portion of the socket wall or base portion are made from a scented material configured to emit a desired scent when heated above room temperature, the scented material having a first rate of vaporization when above room temperature, and a second rate of vaporization when at or below room temperature, the first rate of vaporization being great enough that the desired scent is noticeable in a vicinity of the socket, and the second rate of vaporization being low enough that the desired scent is substantially unnoticeable in the vicinity of the socket, the socket being solid when in the heated state such that the cylindrical cavity remains physically coupleable to the lighting element and the one or more conductors remain electrically and operatively coupleable to the lighting element.

12. The device of claim 11 wherein the socket is made from a material comprising a polymer and the scented material.

* * * * *